United States Patent [19]
Winters

[11] Patent Number: 5,680,875
[45] Date of Patent: *Oct. 28, 1997

[54] DENTAL FLOSS DISPENSER

[76] Inventor: Steven Nebeker Winters, 2605 Commonwealth Ave., Salt Lake City, Utah 84109

[*] Notice: The term of this patent shall not extend beyond the expiration date of Pat. No. 5,573,022.

[21] Appl. No.: 548,217

[22] Filed: Oct. 25, 1995

Related U.S. Application Data

[63] Continuation-in-part of Ser. No. 329,217, Oct. 26, 1994, Pat. No. 5,573,022.

[51] Int. Cl.⁶ ................................................. A61C 15/00
[52] U.S. Cl. ...................... 132/324; 132/325; 132/326; 132/323; 132/329
[58] Field of Search ............................ 132/321, 322, 132/323, 324, 325, 326, 327, 328

[56] References Cited

U.S. PATENT DOCUMENTS

| | | | |
|---|---|---|---|
| 3,311,116 | 3/1967 | Foster | 132/325 |
| 3,393,687 | 7/1968 | Whitman | 132/323 |
| 3,696,821 | 10/1972 | Adams, IV | 132/324 |
| 3,901,251 | 8/1975 | Johnston | 132/326 |
| 4,050,470 | 9/1977 | Miller | 132/323 |
| 4,396,375 | 8/1983 | Gores | 433/141 |
| 4,403,625 | 9/1983 | Sanders et al. | 132/323 |
| 4,679,577 | 7/1987 | Fourie | 132/325 |
| 4,926,820 | 5/1990 | Weam | 132/323 |
| 5,199,452 | 4/1993 | Cheng | 132/323 |
| 5,503,168 | 4/1996 | Wang | 132/323 |

*Primary Examiner*—Gene Mancene
*Assistant Examiner*—Philogene Pedro
*Attorney, Agent, or Firm*—Workman, Nydegger & Seeley

[57] ABSTRACT

A dental floss dispenser having a floss securement mechanism to secure the dental floss with respect to the dispenser body and for use during flossing is provided. One embodiment locks a freely rotating internal spool of dental floss relative to the dental floss dispenser. Both the floss securement mechanism and the spool locking are actuated by the hand holding the dental floss dispenser. The dental floss dispenser may also incorporate a finger grip so that the dispenser can be held by the lower fingers, a contoured shape to better fit the hand of the user, a wide or weighted base for easy pick-up, or a U-shaped indentation for quickly grabbing dental floss at the commencement of flossing. The dispenser is further designed to be used during the flossing procedure as an anchor for the dental floss to thereby allow the user to floss without wrapping floss around at least one finger. The dispenser can also be used with a tool for taking up the used floss during the flossing procedure which allows effective flossing without wrapping floss around fingers altogether. By using the dispenser itself in the flossing procedure, time is saved and flossing becomes more convenient and efficient.

22 Claims, 11 Drawing Sheets

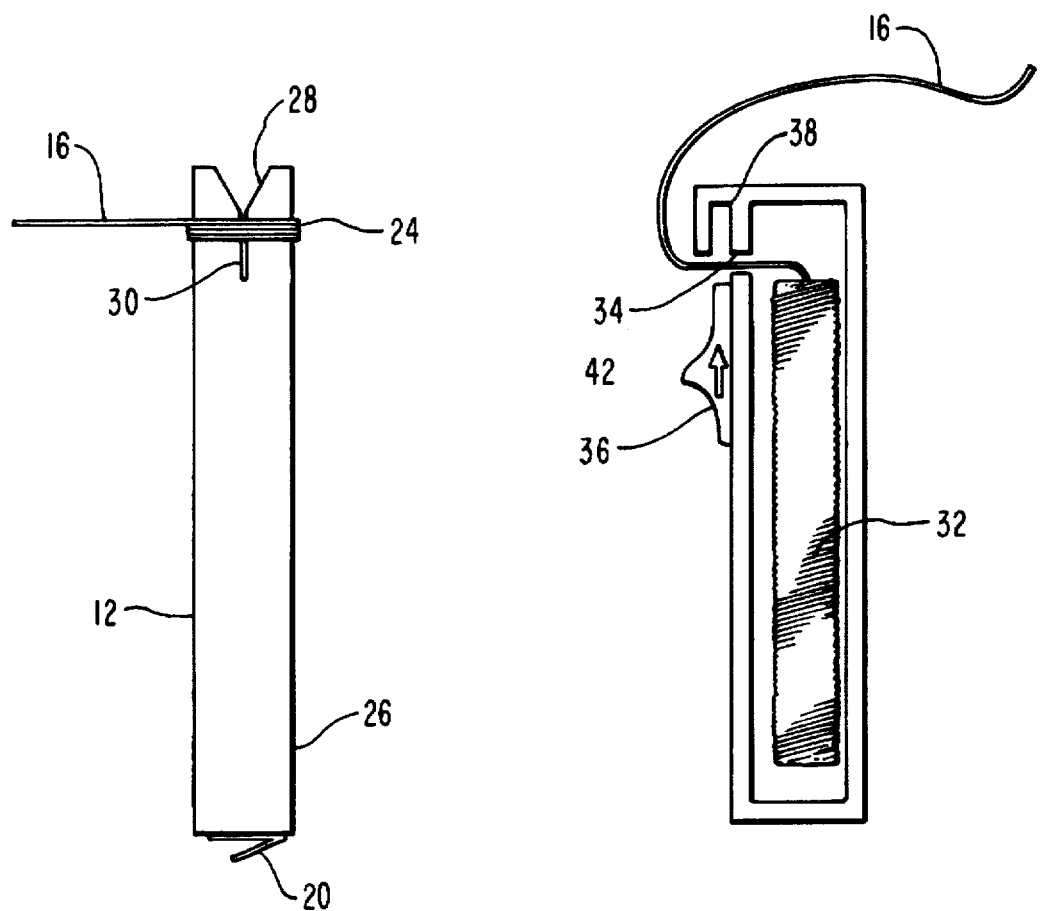
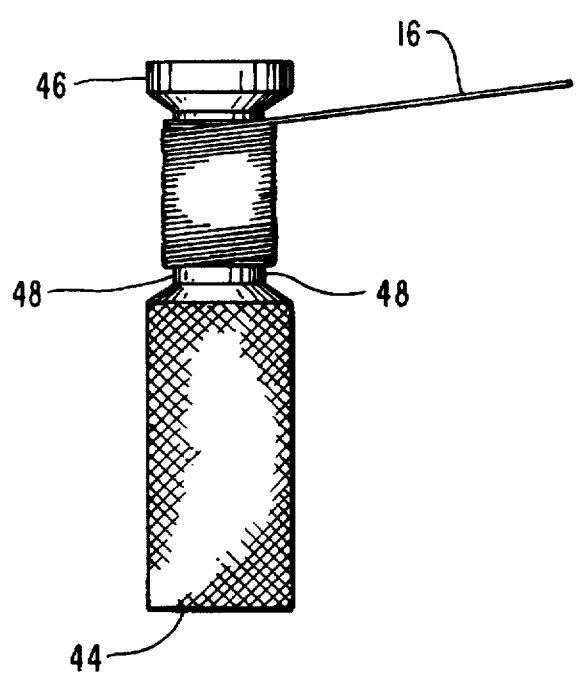

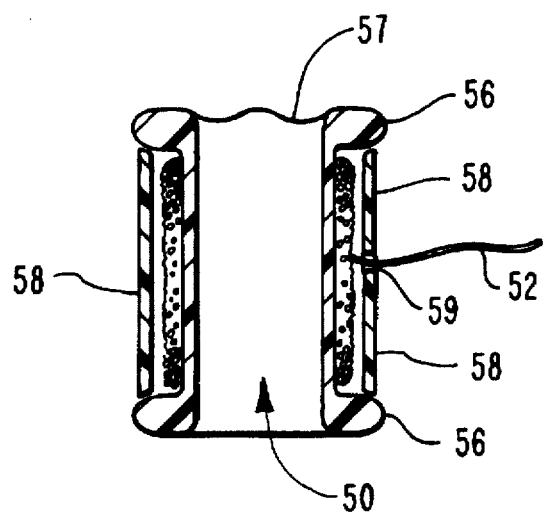
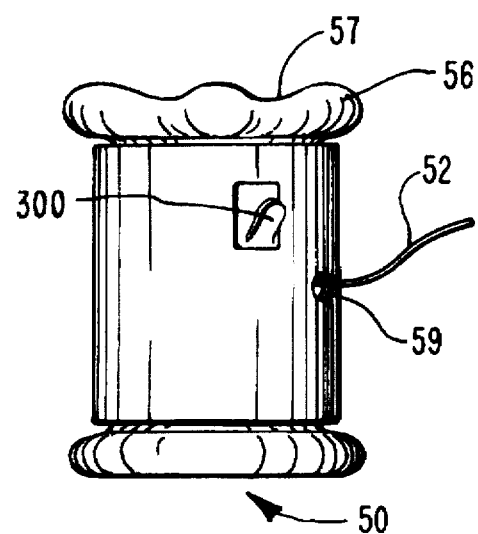
FIG. 8A            FIG. 8B
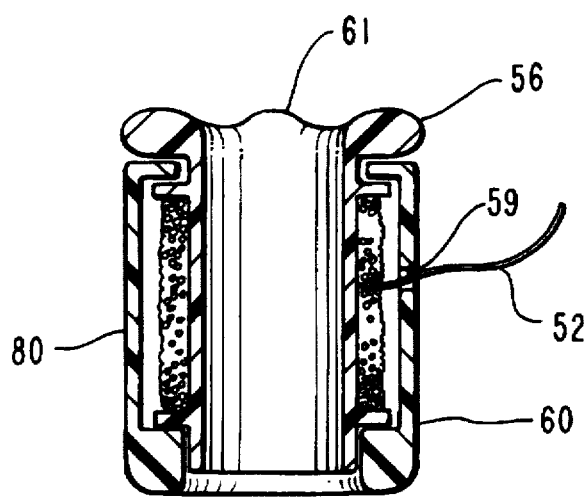
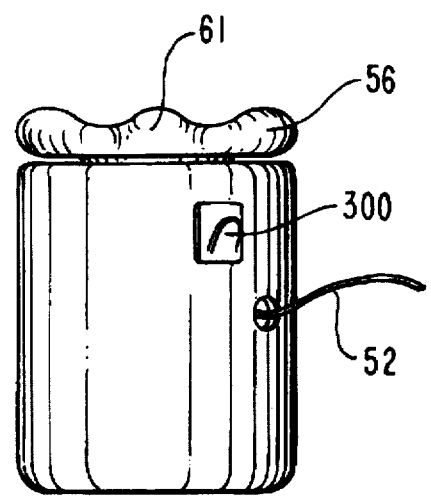
FIG. 9A            FIG. 9B

DENTAL FLOSS DISPENSER

RELATED APPLICATIONS

This application is a continuation-in-part of patent application Ser. NO. 08/329,217 filed Nov. 26, 1994, now U.S. Pat. No. 5,573,022.

BACKGROUND OF THE INVENTION

1. The Field of the Invention

The present invention relates to tools, assemblies, and apparatus that aid in the dental flossing process and more particularly to those tools or devices that require the use of both hands to operate while leaving the thumb and forefingers free to guide the floss between the teeth or to wipe or brush tooth surfaces. This category of device uses the fingers of the person applying the dental floss to guide and provide the "brushing" action of the dental floss.

Specifically, the present invention treats novel dispensers of dental floss where the floss is incrementally dispensed and the rate of dispensing is controlled by one hand of the user. Furthermore, once dispensed, the floss is not cut from the dispenser but loaded in place with respect to the dispenser, so that the dispenser itself becomes part of the flossing process.

2. Present State of the Art

Daily flossing has been proven to be an effective and preferred method of oral hygiene when combined with brushing after meals. Some of the benefits that accrue from flossing are healthy teeth and gums, and prevention of tooth decay.

Dentists continuously and vigorously endorse flossing as an integral part of oral hygiene; yet, there continues to be resistance by the public to floss on a regular basis. The process of flossing requires that a strand of dental floss be considerably tensioned and then forced between the teeth. The tensioned floss is then rubbed along the sides of the teeth beneath the gum line thereby using friction to remove plaque. Additionally, food particles and other debris are quickly and easily removed by this action.

Flossing can be done without the aid of tools. This is accomplished by taking a length of dental floss and coiling or wrapping the floss around both index fingers leaving approximately two to four inches between the fingers. With the floss thus coiled, a person may tension the dental floss by pulling the fingers apart. Using the thumb and the index finger, the user may guide the floss to the desired location in her mouth. The index finger and thumb are used to guide the floss in between the teeth. A fair amount of force is necessary to drive the floss in between the teeth.

The forces of keeping the floss tensioned and driving the floss between the teeth tends to cause pain in the index fingers where the dental floss is tightly coiled. A user may even find it necessary to interrupt the flossing process entirely in order to loosen the floss from around the fingers to restore blood flow.

Another common problem is excess waste of dental floss. When wrapping floss around the fingers, a certain excess amount must be used in order to provide enough coils so that the floss will tighten when tensioned. Furthermore, a person is likely to overestimate rather than underestimate the total amount of floss needed.

Yet another problem that is commonly encountered is the awkward nature of advancing the floss so that fresh, unsoiled floss is used against the tooth's surface. A fair amount of disruption occurs when floss is advanced from one finger to the other and then retensioned thus making the floss ready for continued flossing. The overall effect is to increase flossing time, waste floss because of lack of control in how much floss gets advanced, and frustrate the user due to general inconvenience.

Various devices and assemblies have been proposed to overcome these problems of flossing associated with proper dental hygiene. With all of the below mentioned devices, the forefinger and thumb continue to be used to guide and control the tensioned dental floss. While all of them are effective at reducing the pain involved with winding the floss around the forefingers, they have varying degrees of success dealing with the other above-mentioned problems. Furthermore, none are designed to dispense the dental floss and remain connected to the dental floss to assist in the flossing process itself. These devices include U.S. Pat. No. 3,393,687 to Whitman, U.S. Pat. No. 4,403,625 to Sanders, U.S. Pat. No. 3,696,821 to Adams, and U.S. Pat. No. 4,050,470 to Miller.

The Whitman applicator provides for one end of the floss to be connected to the applicator while the other end is held by the hand not holding the applicator. Though this applicator effectively may solve the problem of finger pain, it requires a fair amount of effort to thread and set it up for use. Furthermore, the free end of the floss may have to be wrapped or coiled around the finger in order to allow proper tensioning and guidance. Moreover, it does not allow the user to incrementally move the floss strand to get fresh floss without the burdensome process of unthreading and cutting the existing floss strand and then rethreading the applicator with a new strand of floss. Additionally, another supply of dental floss is needed.

Sanders discloses a disposable hygienic device that acts both as a toothpick as well as a flossing tool. The problem of the pain in the index fingers due to the wrapped floss is solved, but there is no provision for using a continuous strand of floss since the Sanders device is disposable; it is not designed to accommodate new strands of floss. It further fails to incrementally use the floss in a manner that leaves no wasted floss. The effective area of usable floss is relatively small and is likely to become extremely soiled. It also appears that the two pieces that form the handles or the grasping means of the device are very small thereby making it somewhat difficult to grasp. Again, there is no sizeable supply of floss that can be used.

Adams discloses a pair of thimble like devices to fit over the tops of the index fingers. This allows control and proper tensioning of the floss while protecting the index fingers from painful floss winding. However, moving to a fresh piece of floss is an awkward proposition since one must loosen the thimbles in order to move the floss. Furthermore, the amount of tension created by this method may be less than optimal. It would likewise be wasteful, since users would likely prefer to pull enough floss between the thimbles so that soiled floss is not in contact with the fingers. Yet again, another supply source is needed to dispense the floss.

Miller discloses an assembly that is used like the present invention with the exception of fresh floss advancement. Finger pain is eliminated but moving the strand of floss in order to place a fresh, unsoiled piece of floss next to the tooth requires disconnecting one of the two members and reconnecting it elsewhere. This is a clumsy process that would be time consuming and wasteful of floss. As with the other disclosures, a completely difference source for the floss is required.

None of the previous devices effectively solve the problem in the art of easily transporting a strand of floss such that fresh unsoiled floss can be placed for use in cleaning the teeth. The various ways of repositioning fresh floss in the above-mentioned patents are all unwieldy and hinders the task of flossing the teeth. Furthermore, none of them conveniently store a large quantity of dental floss and supply the floss as needed. This in turn makes the chore of daily flossing an oppressive and time consuming operation.

In addition, the above-mentioned ways of advancing the floss tend to be relatively wasteful of the floss. They all leave significant quantities of the floss in a clean and unused condition. The awkwardness of the advancement mechanisms tends to affect the user negatively in that she will tend to continually floss with soiled floss rather than go to the trouble of advancing the floss to get an unsoiled portion of the floss in contact with the teeth thus compromising the quality and effectiveness of the flossing operation.

SUMMARY AND OBJECTS OF THE INVENTION

It is an object of this invention to provide a floss dispenser that can also be used while flossing thus reducing the time and number of different items needed for effective, convenient, and efficient flossing.

It is an important object of thins invention to disclose a dental floss dispenser and applicator assembly consisting of a dental floss dispenser and an elongated member used as a take-up spool for used dental floss. The floss strung between the dispenser and the member provides the proper tension for flossing. The floss may be incrementally advanced by rotating the take-up spool member and releasing the dispenser locking mechanism to dispense floss from the dispenser. This can be done without the necessity of retensioning the floss or otherwise significantly interrupting the flossing process. A user's finger may constitute the "take-up" spool member as it is explained throughout the application.

Moreover, the dispenser may be a simple spool designed to fit around a finger. In this configuration, the user would let the floss rotate freely from the spool when advancing dental floss. The floss is tensioned by bending the finger thus grasping the source spool. The floss on the spool may be exposed or covered by a sleeve.

Furthermore, the floss source is preferably a dispenser that is specifically designed to be held in the palm of the hand during flossing. The dispenser has a locking mechanism which is activated when the hand is closed around the dispenser. The locking mechanism is a means of securing the floss itself with respect to the dispenser body or a means for locking a spool with respect to the dispenser body. The closing of the hand causes a member to move against and hold the spool which, in turn, holds the floss providing the needed tension in the extruding strand of floss or the member moves directly against the floss or floss strand. When the hand is opened, the member moves such that the spool or floss strand is released and the floss can be advanced. Various different means may be used to accomplish the locking action. A number of such means will be explained and others will be apparent to those skilled in the art.

Alternatively, the present invention can be configured so that the opposite operation of the locking mechanism can occur. For example, the natural state of the mechanism could be in the locked position and require the user to close the hand in order to release the floss. In such a case the member mentioned above will hold the spool in a fixed position until disengaged by the user.

Tightening the hand around the dispenser to produce tension in the strand and the opening of the hand to advance the strand are actions which fit comfortably into the normal flossing procedure. Furthermore it frees the more dexterous fingers by allowing them to be used only for manipulating the floss strand between the teeth while the less dexterous lower fingers are solely employed for alternately advancing the floss strand. Flossing time is greatly reduced because the device allows each finger to be fully utilized for the task for which it is most suited. The source dispenser also has slots or gripping means in which fingers are inserted to provide stability when the hand is opened for advancing the floss.

The preferred floss dispenser doubles as a tool to aid in flossing and the floss stays connected to the dispenser until after flossing is completed. This tool aspect of the dispenser provides substantial benefit to the user regardless of whether a take-up member is used or whether "take-up" is accomplished in the conventional manner using finger on the hand opposite of the one holding the dispenser/tool.

Another important object of the invention is to provide an easy way of advancing the strand of floss. The rotational scheme used whereby floss is rotated from a source dispenser onto a take-up spool is easily accomplished with the fingertips. The cross-section of the take-up spool can be round or have three or more sides. A square cross-section with only an extremely slight rounding of the edges has proven to be one of the designs which can be easily rotated in the palm using the fingers. It does not necessitate any cumbersome repositioning of the devices or movement of the hands. In this way, total floss time will be shortened and the entire process more enjoyable.

It is a further object of this invention to reduce dental floss waste. Since floss is not wrapped around the index fingers, it is unnecessary to cut off more floss than will be used simply to get the proper tensioning for the flossing process. Secondly, the rotational scheme allows the floss to be advanced incrementally thereby efficiently utilizing nearly the entire quantity of the floss by placing it in direct contact with the teeth to be cleaned at one time or another. Thirdly, the floss can be advanced by an increment equal to the side width of a square rod. If the take-up spool has sides which are a half inch in width, a quarter turn of the rod will only advance the floss a half inch. When floss is directly wrapped around the finger, the only possible advancement length is the circumference of the finger which for adults can be one and one half inches up to two and one half inches. Being forced to advance by such long increments causes a lot of the floss to be unusable.

Yet another object of this invention is to allow the user greater flexibility in choosing the length of working floss. Through being able to increase or decrease the length of working floss by finer increments, the user can continuously alter the length to change the working length and maintain the most comfortable working length while working from the back of the mouth which generally requires longer lengths to the front which requires shorter lengths.

A further object of this invention is improved flossing of the teeth. This is accomplished by allowing more new and unused floss to be subjected to the tooth surface. Fresh, unsoiled floss is a more effective cleaning tool.

A further object of this invention is to reduce the amount of time required for flossing. Using the hand held dispenser and the finger spool the time required for wrapping the floss around a finger is eliminated. As soon as the dispenser is placed in the hand and the floss is inserted in the notch or around the protruding knob on the take-up spool and the take-up spool is rotated once or twice, the individual is ready to begin flossing. This preparation can be accomplished in less time than the standard process which entails removing the floss from a dispenser, cutting it then wrapping it around one finger on each hand (usually index fingers).

Yet a further object of the invention is to eliminate the pain associated with flossing caused by tightly winding dental floss around the index fingers. Since the means of support for the tensioning can be the floss dispenser and take-up members, stress on the fingers is reduced. Even if the floss dispenser is used with a finger to take up used floss, the pain in even that one finger is reduced due to solid and stable nature of tensioning against the dispenser rather than another finger.

These and other objects and features of the present invention will become more fully apparent from the following description and appended claims, or may be learned by the practice of the invention as set forth hereinafter.

While relatively specific embodiments of the rotational dental floss holder and assembly are disclosed with the accompanying drawings, it will be understood that variations and other assemblies will occur to those skilled in the art.

Additional objects and advantages of the invention will be set forth in the description which follows, and in part will be obvious from the description, or maybe learned by the practice of the invention. The objects and advantages of the invention maybe realized and obtained by means of the instruments and combinations particularly pointed out in the appended claims.

To achieve the foregoing objects, and in accordance with the invention as embodied and broadly described herein an improved dental floss dispenser adapted to aid in the flossing process is provided.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawing depict only typical embodiments of the invention and are not therefore to be considered to be limiting of its scope, the invention will be described and explained with additional specificity and detail through the use of the accompanying drawings in which:

FIG. 3 is a side view of one of the take-up spool member of FIG. 1;

FIG. 4 illustrates an alternate embodiment of a dental floss dispenser member where a spool of dental floss is contained within the member;

FIG. 5 depicts another embodiment of a dental floss dispenser member where a large amount of floss is spooled around the member so the user does not have to load the source spool.

FIG. 8a shows a cutaway view of another embodiment of a dental floss dispenser with a freely rotating sleeve covering the floss. The spool rotates on the finger while the sleeve is held in place by the taut strand of floss which extrudes from the hole.

FIG. 8b shows a non-cutaway view of the dispenser of FIG. 8a having a freely rotating sleeve.

FIG. 9a shows a cutaway view of another embodiment of a dental floss dispenser with a sleeve which rests against the base of the finger. The spool rotates within the sleeve but can still be held by bending the finger and exerting force on the top portion of the spool.

FIG. 9b shows the exterior view of the dispenser of FIG. 9a with a sleeve which rests against the base of the finger.

DETAILED DESCRIPTION OF THE PREFERRED EMBODIMENTS

Figure 1:
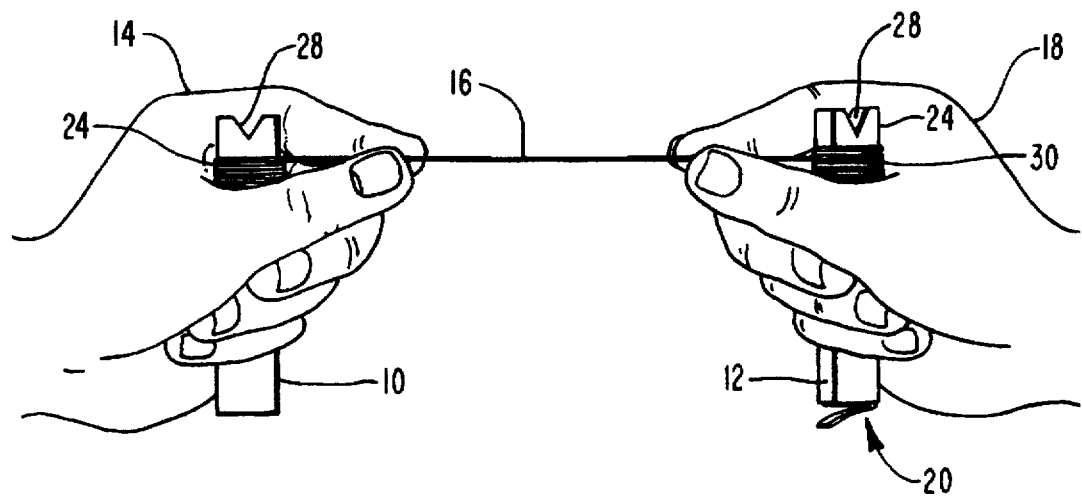
FIG. 1 is a perspective view of one embodiment of a rotational dental floss holder and applicator assembly, illustrating the manner in which an elongated source spool member becomes a temporary dispenser of dental floss through wrapping a length of floss around the elongated member before arming the assembly for use. The temporary dental floss dispenser is grasped by one hand of the user with the dental floss stretched towards the take-up spool member which is held by the other hand of the user during the use thereof with the thumb and index finger of each hand left free to manipulate the floss between the teeth.

One embodiment of a rotational dental floss holder and applicator assembly is shown in FIG. 1 of the drawings, and includes a pair of separate and nearly identical elongated spool members 10 and 12, which members are held apart and contain a strand of dental floss 16 between them to be used for flossing. Furthermore, one member serves as a temporary dental floss dispenser member 10; being a source of dental floss as it is rotated towards the other member. Likewise, the second member serves as a take-up spool member 12, receiving dental floss from the source spool member as it is rotated therefrom.

One important aspect of the present invention is that the dental floss dispenser is also used as a tool to assist in the flossing itself. This is achieved by leaving the floss connected to the dental floss dispenser rather than cutting it from the dispenser and wrapping it around the fingers as is the current practice. By leaving it connected to an appropriately shaped dispenser, and locking it into place, the dispenser serves as an anchor point that allows at least one hand to be free of being wrapped by the dental floss. Furthermore, convenience is enhanced and time is saved because the user eliminates the added steps of wrapping the floss around a finger or other object before commencing to floss.

Preferably, the dispenser contains a large supply of floss so that time is saved in the flossing process by simply grasping the dispenser, pulling an amount of floss, and beginning the flossing procedure. However, this need not be the case and this is illustrated in FIG. 1 by using a simple elongated member as a temporary floss dispenser. This is achieved by taking a length of floss from a conventional floss dispenser and wrapping it around the elongated member so that it acts as a floss dispenser throughout the flossing procedure. More elaborate embodiments of the floss dispenser will be explained later but the simplified temporary flossing dispenser member is shown so as to explain the benefits of having an anchoring tool for the dental floss during the flossing procedure.

The temporary dental floss dispenser member 10 is held by hand 14 with the lower three fingers of the hand grasped around member 10 while the thumb and index fingers of hand 14 guide the floss 16 while flossing the teeth. Likewise, the take-up spool member 12 is held by hand 18 with the lower three fingers grasping the member 12 and the thumb and forefingers of hand 18 guiding the floss 16.

It is important to realize that the direction of transversal of floss 16 is unimportant. It may go from right to left or from right to left depending on the convenience of the user. In the illustrations, the left hand 14 is pictured holding the temporary dispenser member 10 while the dental floss 16 is traversed to the take-up spool member 12 being held by the right hand 18. Again, this is simply illustrative and the spools could be reversed having the floss 16 traverse from left to right with no appreciable change in the invention.

Spool members 10 and 12 are essentially identical with the exception that spool member 12 has a cutting utensil 20 for cutting the floss after use (to discard it). The cutting mechanism 20 could be attached or constructed into either member 10 or 12 at virtually any location. It is shown as an example for convenience during the flossing process.

Take-up spool member 12 is examined in more detail in FIG. 3 and illustrates the functionality and usage of both members 10 and 12. Once the rotational dental floss holder and applicator assembly is armed and ready as in FIG. 1, it may be used for flossing teeth. A more particular description of how to arm the rotational dental floss holders and applicator assembly as well as the method of flossing the teeth will be explained in more detail hereinafter.

Figure 2:
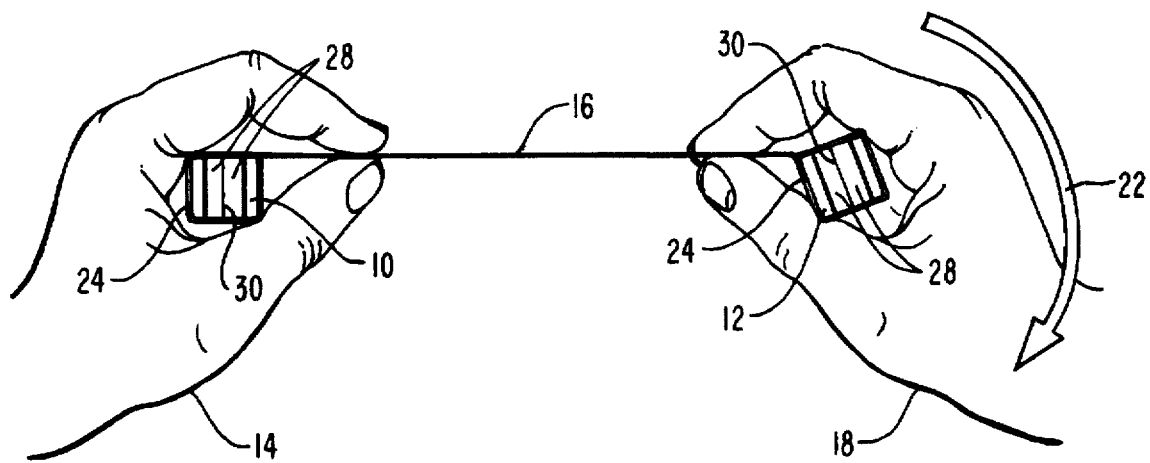
FIG. 2 is a top view of the rotational dental floss holder and applicator assembly of FIG. 1 showing the rotational motion of the dental floss as it rotates from the temporary dental floss dispenser member to the take-up spool member.

FIG. 2 illustrates the rotational operation of the two spool members; one being a temporary dispenser member 10 the other being a take-up spool member 12. The floss 16 will travel from the temporary dispenser member 10 to the take-up spool member 12 as illustrated by the arrow 22. This rotational movement of the floss 16 is accomplished by the fingers of hands 14 and 18, respectively. The hands 14 and 18 rotate the members 10 and 12 in order to cause the floss 16 to travel from the temporary dispenser member 10 to the take-up spool member 12.

This rotational method of causing the floss 16 to traverse between source spool member 10 and take-up spool member 12 is a major improvement over anything before conceived or suggested regarding hand-held flossing tools and assemblies. It allows fresh areas of the floss to be quickly presented for use in the flossing process. It is easy for the user since only manipulation of the fingers is necessary to get the fresh floss ready for contact with the tooth surface. It does not require cutting the floss or repositioning the tool onto another piece of floss in an unwieldy manner as has been exhibited by devices in the prior art. It further provides for efficient use of the floss since there are not big gaps of unused floss that are discarded in the process of positioning the assembly with the fresh floss.

Dental floss as used in this application refers to the thread-like structure that is commonly purchased for cleaning teeth. It also encompasses variations on this material such as dental tape where the floss may be flattened to create a larger surface to be rubbed against the teeth. The term "dental floss" also encompasses any material that can be used in cleaning teeth that is adaptable to being coiled or spooled around the elongated spool members as shown in the drawings and described in this specification.

FIG. 3 shows a more detailed view of an elongated spool member 12; specifically this would be a take-up spool member 12 as illustrated in FIG. 1. The only difference between this take-up spool member 12 and the temporary dispenser member 10 is the cutting device 20 attached to the bottom end 26 of the elongated spool member 12 and the supply of dental floss found on member 10. Additionally, the difference between the temporary dispenser member 10 as illustrated in FIG. 1 and a take-up spool member 12 as illustrated in FIG. 1 and FIG. 3 is that the take-up spool member 12 will be receiving used or soiled floss while the temporary dispenser member 10 will be giving up fresh or clean floss. It is critical to note that a finger alone can still be used as a take-up member for use with a floss dispenser member and still have substantial benefits though some finger pain may be involved.

FIG. 3 shows take-up spool member 12 having a bottom end 26 for grasping by the lower three fingers of the hand and a top end 24 containing a means of fastening a length of floss. This is accomplished by a V-shaped opening 28 in the top end 24 of the take-up spool 12. The V-shape opening 28 tapers to a slit 30 that will secure the floss. The purpose of the V-shaped opening 28 is to channel the floss into the slit 30. When the floss 16 is forced into slit 30, the sides of the slit 30 exert sufficient force upon the floss 16 that is securely anchored.

To arm the rotational dental floss holder and applicator assembly, a length of floss 16 sufficient to floss all of the teeth is cut or otherwise removed from a commercially available standard roll of dental floss. One end of the floss 16 is slid through the V-shaped opening 28 of the top end 24 of the temporary dispenser member 10. Once the end of the floss 16 is firmly lodged in the slit 30, the floss 16 is wrapped around the top end 24 of the temporary dispenser member 10. Once spooled, all of the floss 16 is wrapped around the top end 24 of the temporary dispenser member 10.

The free end of the floss 16 that has been coiled around the top end 24 of the temporary dispenser member 10 is taken and slid down the V-shaped opening 28 on the top end 24 of the take-up spool 12. It is lodged firmly in the slit 30 of the top end 24 of the take-up spool 12. With the hand 14 grasping the temporary dispenser member 10 and the hand 18 grasping the take-up spool 12 the fingers of both hands rotate the respective members 10 and 12 until the floss 16 has traversed from temporary dispenser member 10 to take-up member 12 and has coiled a few coils around the top end 24 of take-up spool 12.

The floss 16 is tensioned by the user pulling the members 10 and 12 away from each other until the desired tension is attained. The forefinger and thumb of hands 14 and 18 are used to guide the tensioned floss 16 into the interproximal spaces between the teeth. The floss 16 can then be rubbed against the side tooth surface or be used to dislodge food particles between the teeth. It can also be used to reach below the gum line as commonly taught by dentists. The fingers of the hands 14 and 18 are free from the pain associated with floss wound around the index finger and better guidance is provided since the floss is tensioned with the members 10 and 12. It is noted that the use of only one of the members can result in substantial reduction in finger pain.

As a tooth is cleaned and the floss 16 becomes soiled the user may use the hands 14 and 18 to rotate members 10 and 12 in such a manner that the floss 16 leaves the source spool member 10 and is taken up or coiled around the take-up spool member 12. This provides fresh floss and hence better cleaning of tooth surfaces.

When flossing is complete, cutting member 20 may be used to sever floss 16 at a point where only fresh floss remains. The soiled floss is then unraveled or uncoiled from the top end 24 of the take-up spool member 12 and discarded.

Those skilled in the art will notice various aids and improvements that can be made on this most basic mode as has been described. For example, texturing may also be placed on the members 10 and 12 to provide a firmer grip. Members 10 and 12 may also be contoured to provide a more sure grip as well. A little "lip" may be placed at the top of spool members 10 and 12 such that the floss will not slip off the members when the members 10 and 12 are moved in a downward fashion.

The fastening or securing means illustrated by the V-shaped opening 28 and the slit 30 are only representative of a simple way of securing the floss 16 for tensioning. This means for fastening the floss to a spool member may be accomplished in a number of ways including but not limited to a clasp, tying it in a knot around the spool member, gluing it, etc. Furthermore, many other ways may become apparent to those skilled in the art. In a simple implementation, the floss may be wound around the member, relying upon the friction of the floss wound upon itself to keep it secure.

Figure 19A:
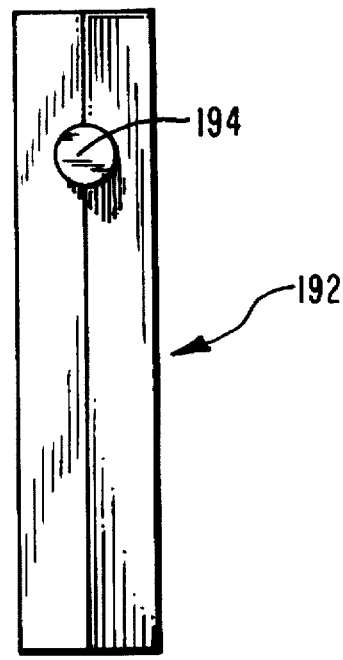
FIG. 19A shows an embodiment of a take-up spool member having a button for securely wrapping dental floss.
Figure 19B:
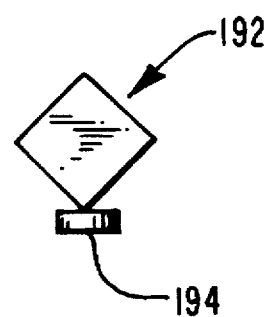
FIG. 19B is a top view of the take-up member shown in FIG. 19A.

FIGS. 19A and 19B shows another means for securing the floss onto a take-up member. In FIGS. 19A and 19B, the source take-up member 192 has a button 194 affixed to the main body of the member. The top view, FIG. 19B, shows how the button 194 can be used to wrap floss around the base thereof to create a secure anchor point.

Figure 21:
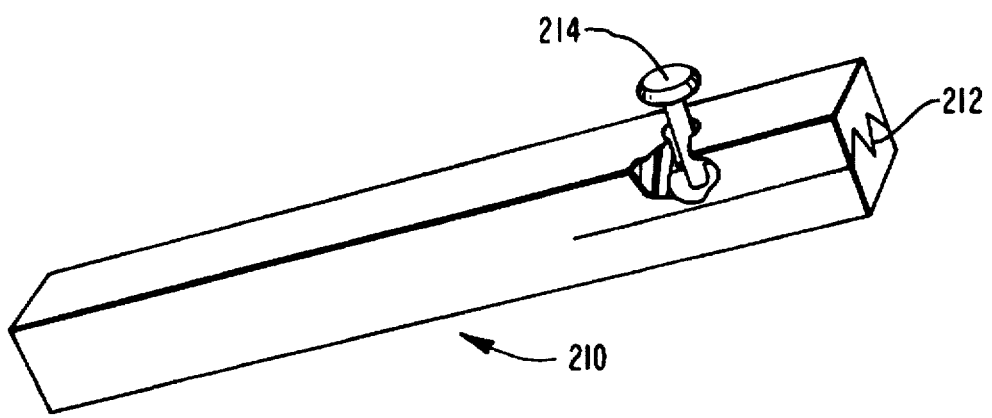
FIG. 21 shows an embodiment of a take-up spool member having serrated and mating jaws for grasping an end of a length of dental floss and a plunger to open the jaws.

FIG. 21 shows a take-up member 210 that has serrated slice 212 that, when separated, will form jaws that can securely grip the dental floss. Plunger 214 shows how the jaws can be opened from the slit 212 to allow the entrance of the dental floss. The natural stiffness of the preferably plastic construction of the take-up member 210 will naturally grip the floss when the plunger 214 is not depressed.

The cutting means 20 is simply a punched metal article creating a sharp edge that is attached to the bottom of a take-up spool member 12. It is similar to the cutting means supplied in a common dental floss dispenser, and could alternatively be attached to the bottom of the temporary dispenser member 10. It could also be attached in a different area rather than the bottom. Furthermore, the cutting means could be a number of different means besides the punched metal mechanism illustrated. For example, a rough edge on a member 10 or 12 could be used to accomplish cutting.

FIG. 4 shows an embodiment of a floss dispenser. FIG. 4 discloses the floss dispenser 40, an internal spool of dental floss 32, a floss exit outlet 34, a sliding switch 36 and a locking switch receptacle 38. A supply of dental floss 16 is held on the internal spool 32 for use with the floss dispenser member 40. The floss 16 exits the floss exit outlet (or dispersal aperture) 34 according to the amount needed for proper flossing. The sliding switch 36 has an open position as shown and a closed position as shown by sliding the switch in the direction of arrow 42. When in the closed position the switch will be firmly placed in the locking receptacle 38 thereby pinching the floss 16. This will provide the fastening means so that the floss 16 may be properly tensioned.

A user would use the fingers of her hand 14 to control the sliding switch 36. When fresh floss is needed the user would slide switch 36 to the open position thereby letting the floss 16 freely travel through the floss outlet 34. The hand 18 would rotate the take-up spool member 12 thereby pulling the floss through outlet 34 from the internal spool 32. Once the floss 16 is properly advanced, the user would use the fingers of hand 14 to close or secure switch 36 into the locking receptacle 38. The floss 16 will then be pinched between the switch and the locking receptacle 38 providing the fastening means for the source spool member 40.

Alternatively, the sliding switch 36 could be spring biased in the closed position (not shown). The user could then simply pull the sliding switch 36 when fresh floss was needed. When the right length had been pulled, the user would release the sliding switch 36 and the spring biasing would spring back to pinch the floss 16 when the sliding switch 36 returned into the locking receptacle 38.

The advantage to having a floss dispenser member 40 as illustrated in FIG. 4 is that a larger amount of dental floss may be contained on the internal spool 32. It can be commercially prepackaged as an alternative to the standard dental floss dispensers now commonly available. It is important to note that floss may simply be packaged inside the source spool member 40 without the internal spool 32.

Using the switching mechanism may be easier for some users rather than manually rotating the source spool member. For example, those with arthritis may appreciate the ease of simply loosening and tightening the sliding switch 36. Moreover, one could envision complex and motorized spool members on both the take-up and/or source spool members. Other variations would include any freely rotatable spool, internal or external along with a way to secure the floss for tensioning.

Yet another alternative for a floss dispenser member is illustrated in FIG. 5. The source spool member 44 is readily adapted for manufacture and represents a prewound source spool member. A large amount of floss 16 is wrapped around the top end 46 of the floss dispenser member 44. The recessed area 48 can be adjusted to accommodate a desired amount of floss to be prewound around the source spool member 44. The end of the floss 16 will be fastened in a commonly used way. For example, it may be stapled to, glued to, molded into, or otherwise attached to the source spool 44. When the dental floss 16 has been totally used from dispenser 44 it can be simply discarded.

The floss dispenser member 44 of FIG. 5 is to be used with the take-up spool member 12 of FIG. 3. This allows the user: (1) to load the take-up spool member 12, (2) floss the teeth, (3) use the rotational method of causing the floss 16 to travel from the source spool member to the take-up spool member, (4) cut the used floss from the source spool member 44, and (5) discard the used floss by unwinding the floss that had been captured by the take-up spool member 12.

An advantage of the floss dispenser member 44 of FIG. 5 is that it is easily and inexpensively adapted for manufacture. It provides an easy mechanism for selling dental floss in this preloaded source spool member. This provides further convenience to the user and greatly enhances the probability that flossing will be done on a regular basis.

It may be noted that the prewound floss dispenser member 44 is simply illustrative and that those skilled in the art will clearly devise other aesthetically pleasing designs but that will encompass the same principal of having dental floss wrapped around an elongated source spool member that can be used as shown in FIG. 1. Additional structure may be added to the floss dispenser member 44 of FIG. 5 that would keep the floss enclosed and protected from the external environment.

Figure 6A:
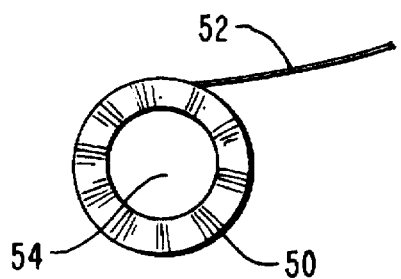
FIG. 6a shows an embodiment of a dental floss dispenser that is placed on the finger of the user. The rotation or advancement of the floss is controlled by gripping the spool. The top of the dispenser has a waved profile to assist in gripping when the finger is bent.
Figure 6B:
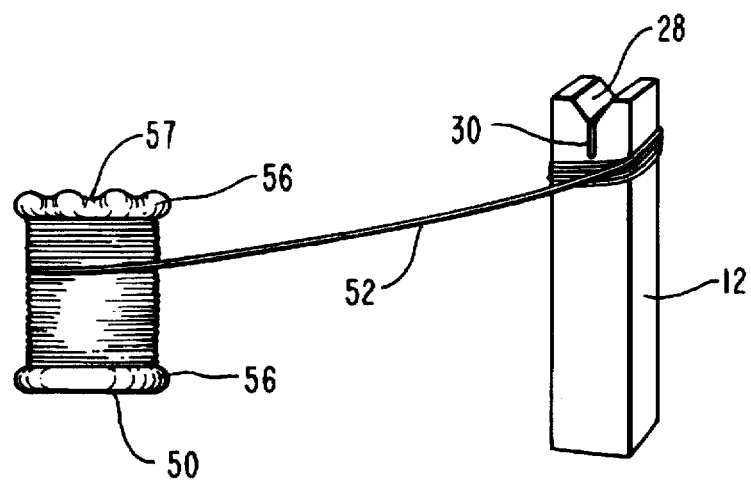
FIG. 6b shows the dispenser of FIG. 6c that is to be placed on a finger in conjunction with a take-up spool.
Figure 7:
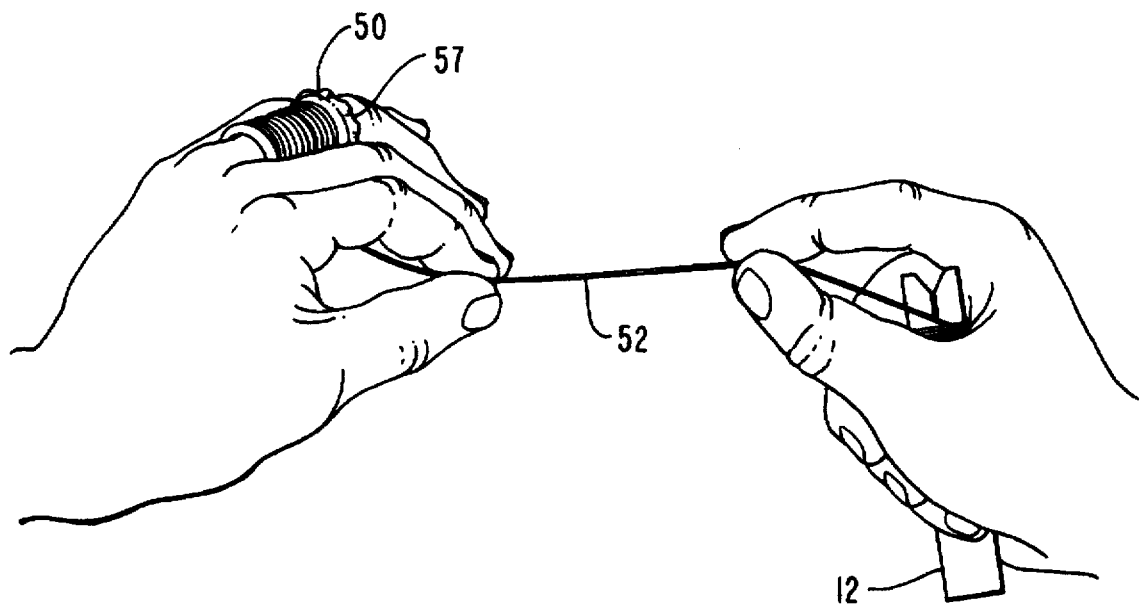
FIG. 7 shows the dispenser of FIG. 6a on the finger of the user and the take-up spool being held in the palm of the other hand.

FIGS. 6a, 6b, and 7 show a floss dispenser that may be placed around a finger, preferably the ring finger, thereby serving as a source spool of dental floss. The spool dispenser 50 has wrapped around it dental floss 52. The spool dispenser 50 has a hollow area 54 for placing the spool around one of the fingers of the hand; preferably the ring finger. When the user desires to advance floss, she loosens the finger and allows the spool to rotate freely around the finger thereby advancing the floss. When the user desires to tension the floss, she merely bends the finger around the spool thereby holding it in a fixed position. The spool dispenser 50 may or may not have flanges 56 to guide and control the floss. The source spool 58 may or may not have waved pattern 57 around the top flange to aid in gripping the spool when the finger is bent. This embodiment of a spool around a finger, as shown in FIGS. 6a, 6b, and 7, provides the advantage being easily adapted for manufacture and allows for the personal preference of the user. Some users will find this spool more comfortable than grasping an elongated member.

FIGS. 8a and 8b show the spool dispenser 50 of FIGS. 6a, 6b, and 7, with a sleeve 58 covering the floss. The sleeve completely covers the floss and can rotate freely around the spool. The floss 52 passes through the sleeve by means of a hole 59 on the sleeve. During use, the tension of floss causes the sleeve to rotate around the spool as floss is dispensed. A punched metal floss cutter 300 may be placed on the sleeve 58.

FIGS. 9a and 9b show another embodiment of a spool dispenser 61 with only a top flange 56. The sleeve 60 rests against the base of the finger and does not rotate. When the finger is loosened, the spool dispenser 61 rotates within the sleeve 60 thus dispensing floss 52 through the hole 59 in the sleeve. A punched metal floss cutter 300 may be placed on the sleeve 60.

Figure 10:
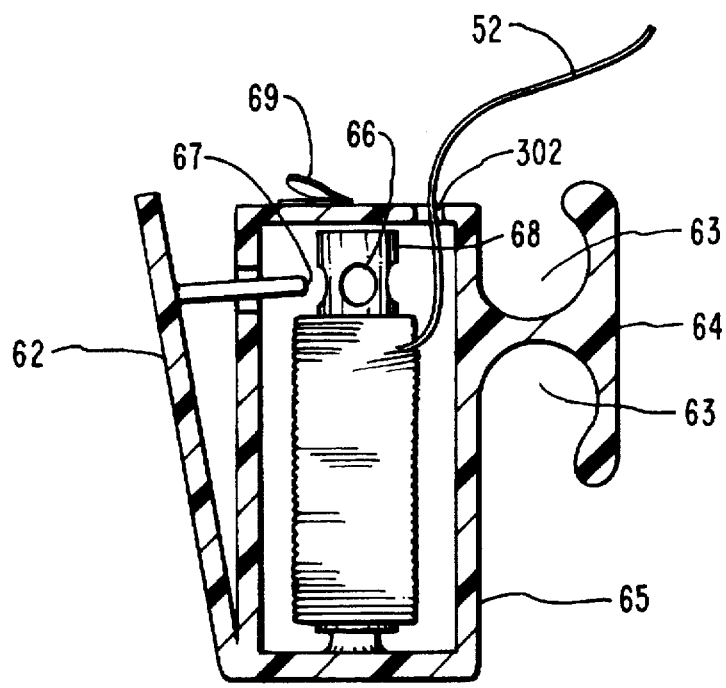
FIG. 10 shows a cutaway view of another embodiment of a dental floss source dispenser with a spool lock implementing locking holes in the released position and the portion which holds two fingers when the dispenser is being held.

FIG. 10 shows a floss dispenser 65 which is held in the hand during flossing. The dispenser of FIG. 10 has a lock member actuator 62 which can be pressed such that it prevents the internal spool 68 of floss 52 from rotating. There are several possible locking mechanisms that can be used and the various examples shown here are illustrative. Many others will be apparent to those skilled in the art and are considered within the scope of the present invention. A locking mechanism will either bind the floss itself with respect to the dispenser body or will lock a spool of dental floss with respect to the dispenser body. In either case the floss will be in condition for tensioning.

FIG. 10 shows the lock member actuator 62 with an attached rod 64 which is positioned such that when the locking member 62 is pressed towards the dispenser 65, the rod 64 moves into one of the holes 67 at the top of the spool 68. Lock member actuator 62 is biased outward from the floss dispenser 65. This locks the spool preventing it from rotating allowing the floss 52 to be pulled to an appropriate working tension. During flossing, two fingers are inserted in the grip area 63 created by a finger grip member 64. The finger grip member 64 holds the fingers firmly in place allowing the user to open his hand to unlock the floss without loosening his grip on the dispenser 65. The dispenser 65 may also have a dental floss cutter 69. Alternatively, the spool and locking means could be so configured that the spool is normally locked unless the user actuates the locking means to release the spool and allow the floss length to be extended.

Figure 11:
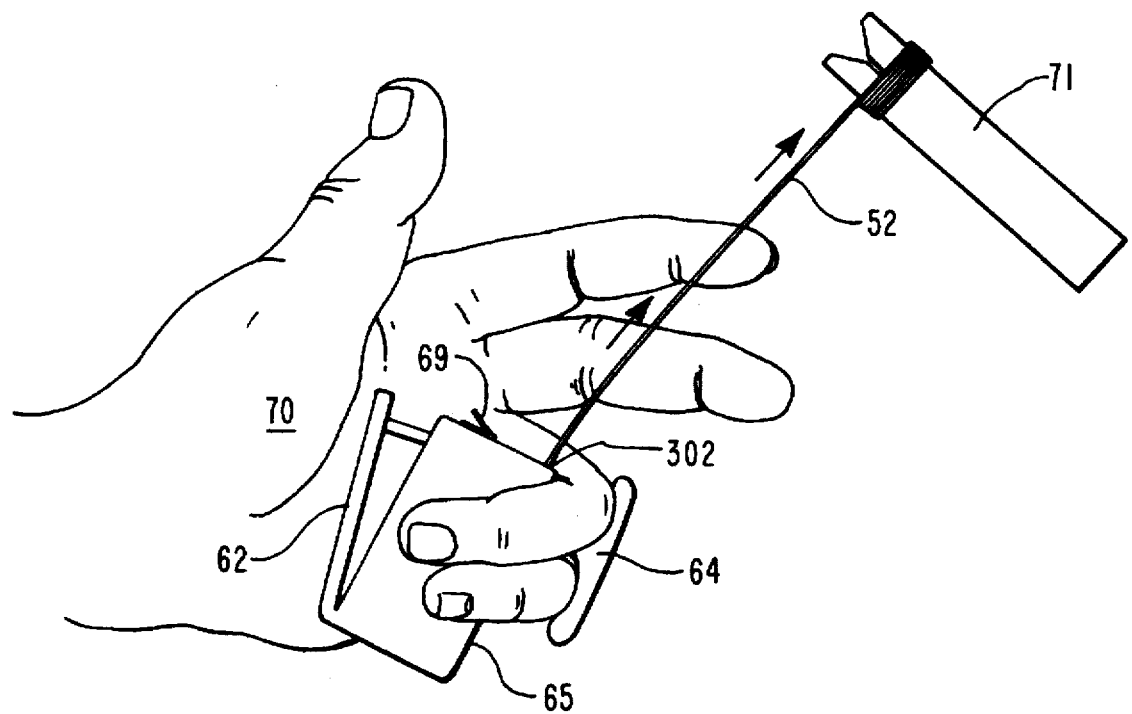
FIG. 11 shows the dispenser of FIG. 10 being held in an open hand and, therefore, the dispenser is in the released position and floss can be advanced.

FIG. 11 shows the hand-held floss dispenser 65 being held in an open hand 70. The lock member actuator 62 is not pressed inward so the floss 52 can be advanced by the take-up spool 71. The finger grip member 64 securely holds the two fingers during the process. While the lower two fingers of the hand hold the dispenser, the thumb and other fingers are free to guide the floss. The floss dispersal aperture 302 is so located so as to facilitate the flossing process. This requires that the aperture be near the guiding fingers, (i.e., thumb and forefinger) which will normally be at the upper end of the dispenser.

Figure 12:
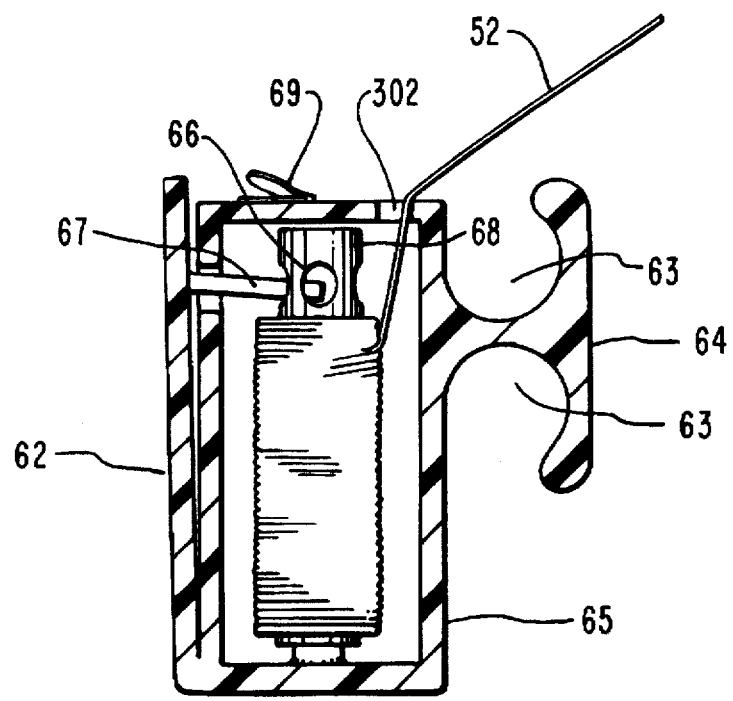
FIG. 12 shows a cutaway view of the dispenser of FIG. 10 in the locked position.
Figure 13:
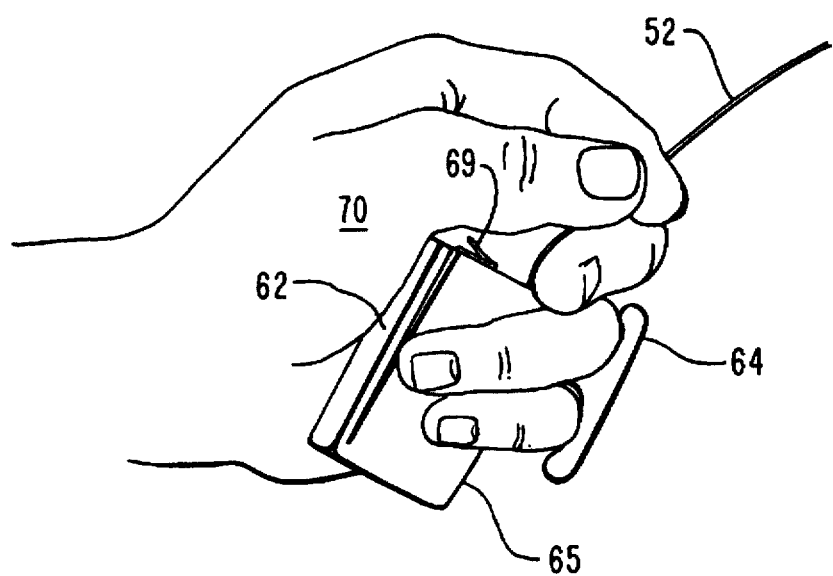
FIG. 13 shows the dispenser of FIG. 10 being held in a closed hand and, therefore, the dispenser is in the locked position and floss can be held taught.

FIG. 12 shows the dispenser in the locked position with the locking member 62 being pressed towards the dispenser 65 thus locking the spool 68 by inserting the rod 67 in the hole 68. The dispenser 65 is in the locked position in FIG. 13 with the hand 70 pressing against the lock member actuator 62. The forefinger and thumb, as well as the index finger if necessary, are free to guide the dental floss 52.

Figure 14:
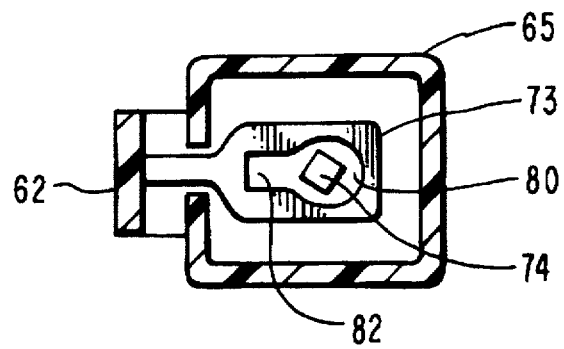
FIG. 14 shows a cross-sectional view of the source dispenser of FIG. 10 with an alternative locking mechanism utilizing a slotted member that engages the parallel sides of the internal spool to hold the spool stationary. The view shows the locking mechanism in the unlocked position. Reversing the position of the locking slot with the open hole can be seen to reverse the operation of the device.

FIG. 14 shows an alternative method for locking the spool. The lock member actuator 62 is pushed in when the hand is closed. The lock member 73 which locks the spool has a round hole 80 which connects to a square slot 82. The spool 68 has a square cross-sectional spool top 74 designed to fit tightly into the square slot 82 of the lock member 73. The spool 68 may have a cross-sectional top 74 in a shape other than a square. For example, a hexagon, octagon, or any other shape having multiple parallel sides that would fit securely in the square slot 82 of lock member 73 would be effective. The more parallel sides on the cross-section top 74, the finer length the floss 52 may be advanced.

Figure 15:
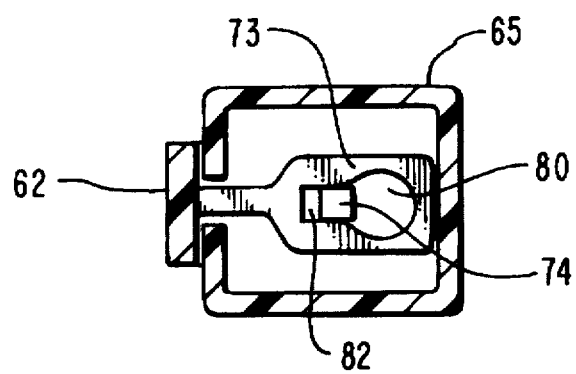
FIG. 15 shows a cross-sectional view of the source dispenser of FIG. 14, but the locking mechanism is in the locked position.
Figure 16:
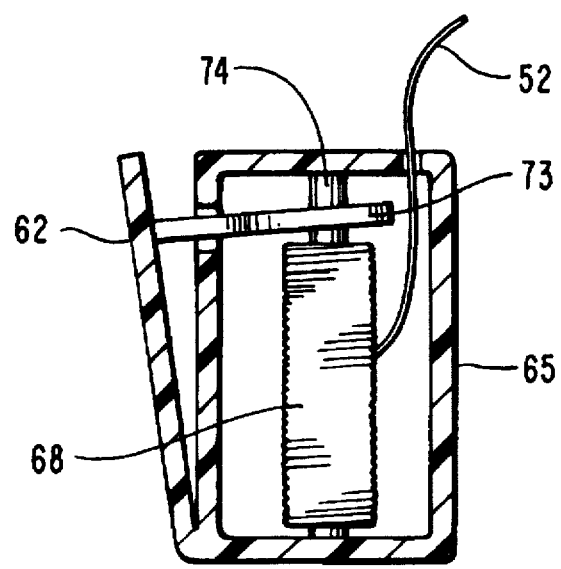
FIG. 16 shows a cutaway side view of the source dispenser of FIG. 14 having the alternative locking mechanism.

When the locking member 62 is not depressed, the spool rotates freely in the circular hole 80. When it is pressed, the spool top 74 locks in the square slot 82 of the lock member 73. In FIG. 15 the spool 68 is locked by having the spool top 74 securely fitted into the square slot 82 of the lock member 73. FIG. 16 is a cutaway view of a dispenser 65 having an alternative locking mechanism as more specifically shown in FIGS. 14 and 15.

One skilled in the art will recognize that with the lock member actuator 62 biased away from the dispenser that the operation of the locking means can be reversed by switching the positions of the square slot 82 and the round hole 80 within the lock member 73. This will leave the floss in the locked position unless the lock member actuator 62 is depressed by the user. This configuration may be advantageous depending on the preferences and abilities of the user.

Yet another way of locking dental floss in a dispenser for proper tensioning is by having the dispenser be made of a squeezable material. As the user compresses the dispenser body, the interior side of the dispenser would come in contact with a freely rotating internal spool of dental floss. As pressure is applied, the spool of dental floss will become locked in a relative position with respect to the squeezable dispenser casing. Once again, many different ways of locking the dental floss will be apparent to those skilled in the art.

The base aspect of all sources of dental floss, whether they be elongated members or spools or variations thereof, is that they provide dental floss that can be readily taken up by the take-up spool member. Furthermore, they must provide a way to tighten or tension the floss so that the floss may be tensioned and proper flossing take place.

FIG. 17A through 17D show a floss dispenser having a quick load feature, knurled hand grips, a stabilizing base, and improved cutting means. The dispenser 170 is preferably molded plastic and has a spool of dental floss 160 residing inside of it. The base 171 is designed to be wide and stable so as to facilitate a user quickly grabbing or releasing the dispenser onto a flat surface with only one hand without tipping the dispenser. Furthermore, the dispenser is molded to fit the lower fingers of the hand of a user as shown at 172. This makes the dispenser easier to grasp and easier to hold during the flossing procedure.

Another feature is the quick-load, U-shaped indentation 174 that allows a user to quickly grab the floss 164 as it is strung between the floss dispersal aperture 173 and the cutting means 178 each located on opposite prongs of the U-shaped indentation. This would be the state of the floss dispenser when the user decides to commence flossing. Once the floss 164 is grasped it can be loaded onto a standard take-up spool as shown in FIG. 20 or the user may simply use the forefinger as a take-up spool as is the conventional practice.

Figure 17A:
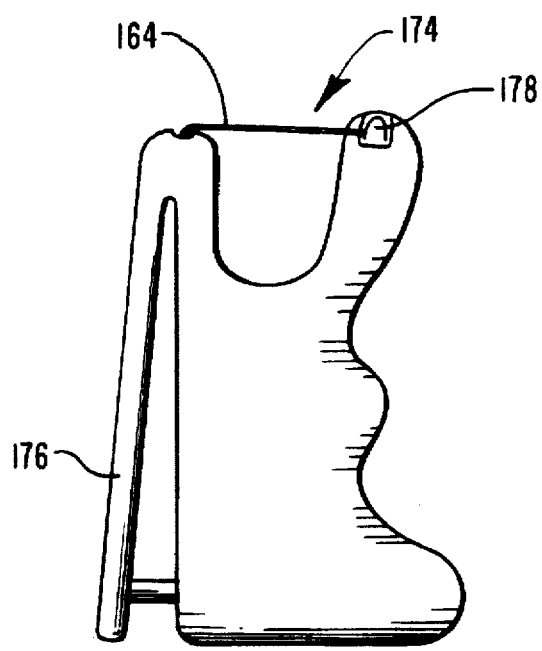
FIG. 17A is a side view of yet another embodiment of an enhanced dental floss dispenser having a contoured body for easy gripping, a dental floss braking means for gradually tensioning the floss, and a deep indentation in the top thereof for easy access to the dental floss.
Figure 17B:
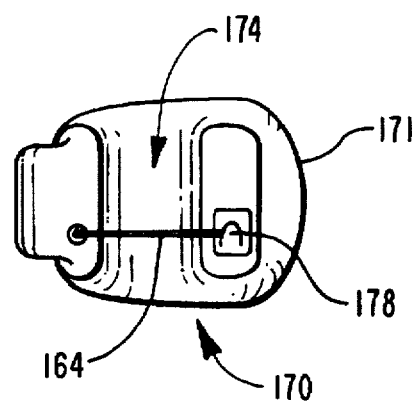
FIG. 17B is a top view of the dental floss dispenser of 17A showing the forward placement of the floss dispersal aperture and the floss cutter.

An added feature of the floss dispenser 170 is the forward placement of the floss dispersal aperture 173 and the cutting means 178 best expressed in the top view shown in FIG. 17B. Such forward placement allows a sloping top edge 175 that will guide the floss into the cutting means 178 when flossing is finished and the user desires to cut the soiled floss from the dispenser to discard it. It is preferable in most embodiments that the floss dispersal aperture 173 be located where it is accessible to the thumb and forefinger that are free from holding the floss dispenser itself. Normally, this will be at the upper end or region of the floss dispenser.

Figure 17C:
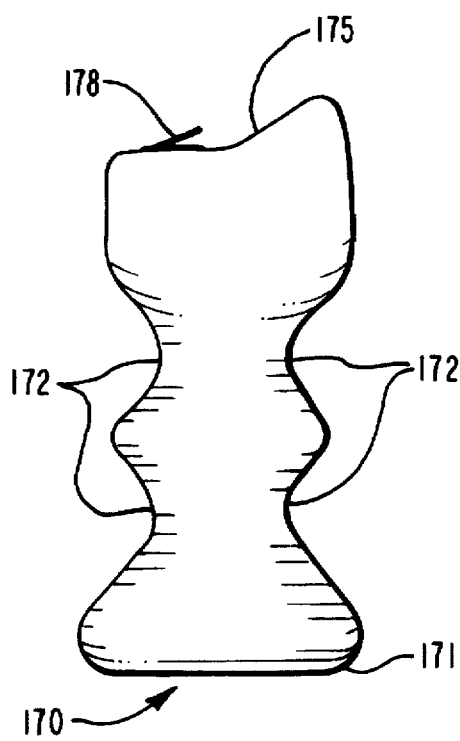
FIG. 17C is an edge view of the dental floss dispenser of 17A showing the body contours and the sloped top that guides the dental floss towards the cutter for easy cutting.
Figure 23:
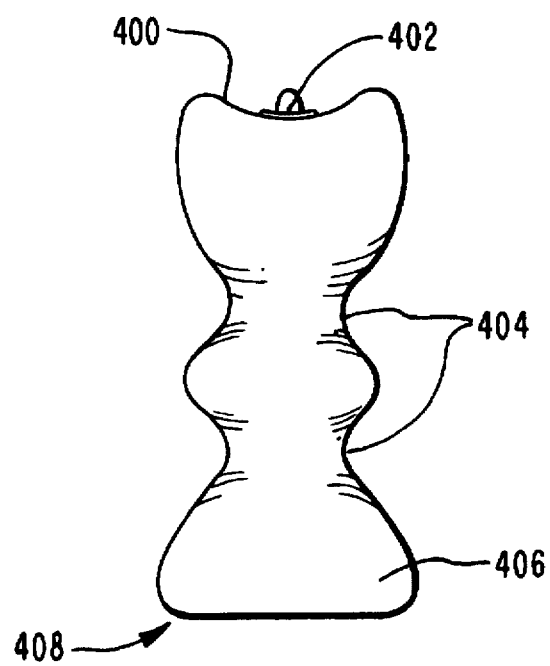
FIG. 23 shows a trough guiding feature that can be added to the dental floss dispenser of FIG. 17A.

FIG. 23 shows an alternative guidance means to be used in conjunction with a U-shaped indentation embodiment. The dispenser 408 is very similar to dispenser 170, of FIG. 17A, having a wide base 406 and contoured grips 404. On the top end, however, the dispenser 408 differs from the dispenser 170. Rather than a single sloping edge 175 and forward placement of the floss dispersal aperture 173 and cutting means 178 as shown in FIGS. 17B and 17C, dispenser 408 of FIG. 23 utilizes a trough 400 on each prong of the U-shaped indentation. Both the curing means and the floss dispersal aperture are at the lowest point of the trough 400. This provides added benefit in that the dental floss dispenser 408 can be equally accessible to both the right and left hands according to user preference. Furthermore, the upper edges of trough 400 will protect a user from inadvertently injuring herself on the cutting means 402.

Figure 20:
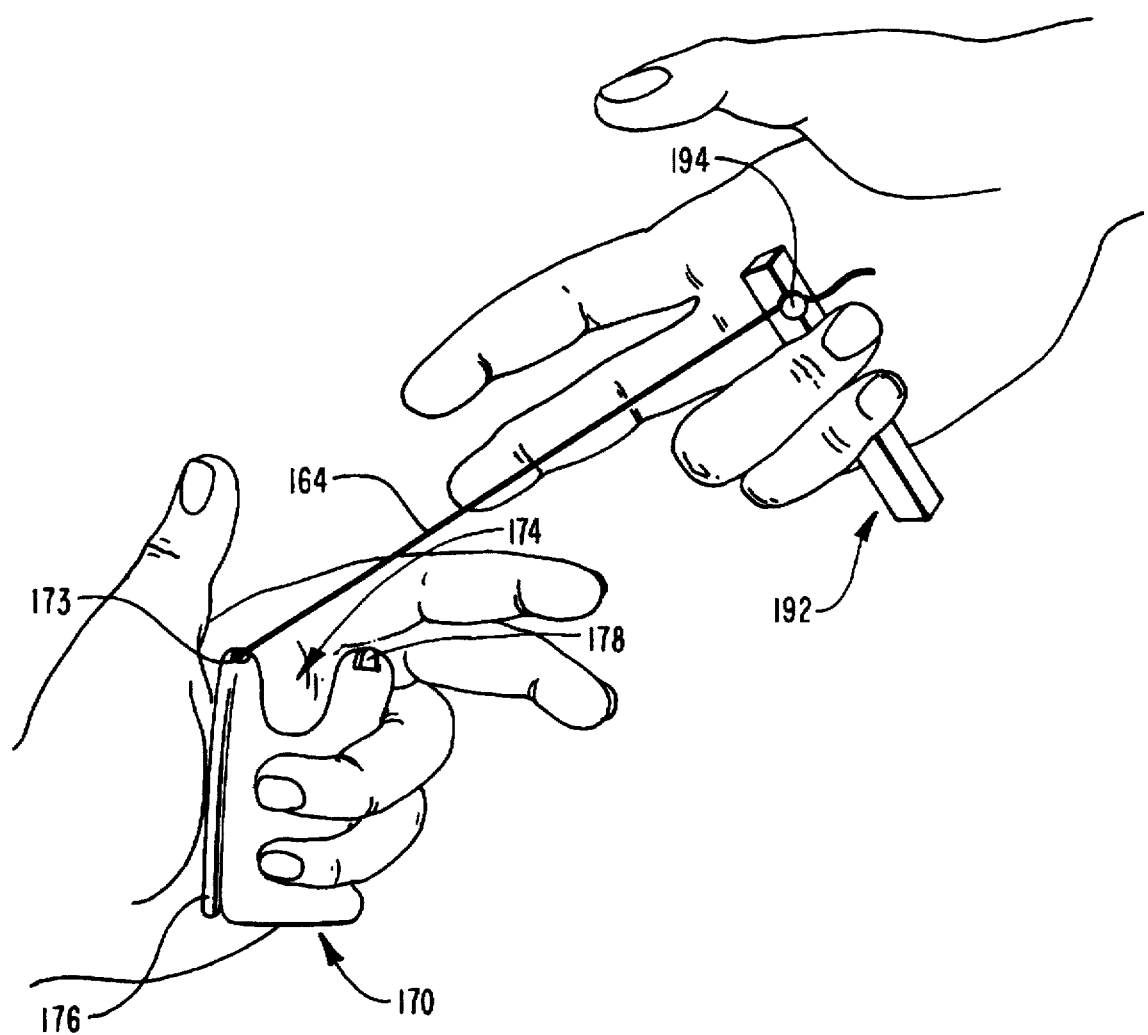
FIG. 20 shows the dental floss dispenser of FIG. 17A in the locked position and armed for flossing with the take-up spool of FIG. 19A. The dispenser is in the locked position so that the floss can be tensioned between the dispenser and the take-up member.

FIG. 20 shows the floss dispenser in the locked position with the user depressing the hand actuated floss securement means to lock the internal floss 160 from moving with respect to the floss dispenser 170. Furthermore, the take-up member of FIG. 19A is shown with the floss properly tensioned between the dispenser/member and the take-up member and readied to begin the flossing procedure.

Figure 17D:
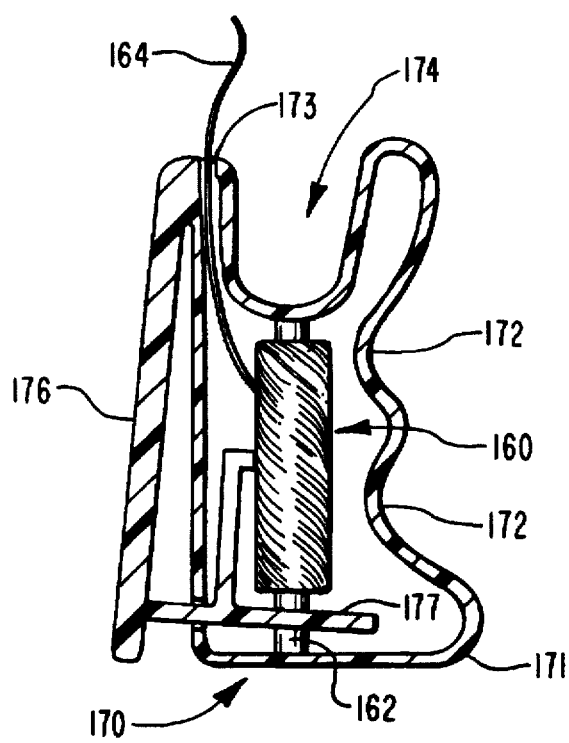
FIG. 17D is a side cut-away view of the dental floss dispenser of FIG. 17A showing the internal workings of the braking means and the ultimate locking means.

FIG. 17D shows the internal workings of the hand actuated floss securement means 176 with hand actuator connected to a slotted member 177 to interact with the spool end 162 of the internal spool of floss 160. The floss securement means operates by providing spool locking means when the spool 160 is locked with respect to the dispenser body, the floss 164 is also secured and ready for tensioning. The spool end 162 is made up of multiple parallel sides to be engaged by the slot of slotted member 177 as was explained in the floss dispenser disclosed in FIGS. 14-16. Furthermore, attached to the slotted member 177 is a braking member 179 that will rub against the spool of floss 160. As the hand actuated floss securement means hand actuator 176 is depressed, the braking member 179 frictionally engages the internal spool of floss 160 to provide graduated tension before the internal spool of floss 160 is tightly locked by the slotting member 177.

Figure 22:
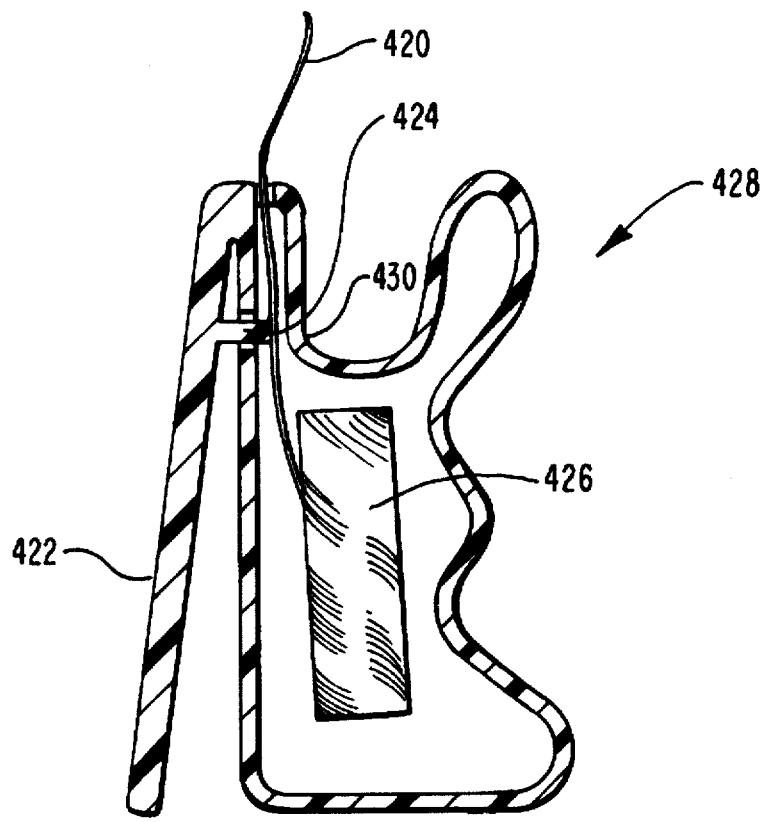
FIG. 22 depicts a cut-away view of the dental floss dispenser of FIG. 17A where the floss is pinched and secured rather than the rotating spool.

FIG. 22 shows the dispenser 170 of FIG. 17D with alternative floss securement means. Rather than lock the spool to secure the floss 420 in place, the dispenser 428 of FIG. 22 locks the floss 420 itself against the dispenser body wall 430. The securement actuating handle 422 has a pinching pin 424 attached thereto. When the actuating handle 422 is depressed, it forces the pinching against the dispenser body wall. The pinching pin 424 is so positioned that it must interact with floss 420 when the actuating handle 422 is depressed. In this manner the pinching pin 424 will secure the floss 420 against the dispenser body wall 430.

Again, as with the embodiment in FIGS. 14-16, the floss securement means operation may be reversed. By changing the location of the slot and the round hole of the slotted member 177, the floss will normally be tensioned unless the hand actuator 176 is depressed to allow the internal spool of floss 160 to spin freely. By biasing the hand actuator 176 away from the floss dispenser, user interaction is required to change the floss from one state to another and this arrangement allows the "normal" state to be chosen at manufacture whether locked or unlocked.

Figure 18A:
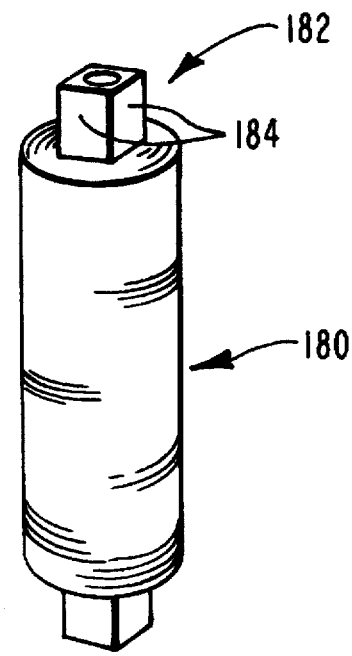
FIG. 18A shows an embodiment of an internal spool or replacement spool of dental floss having squared ends to be used with a slotted locking member.
Figure 18B:
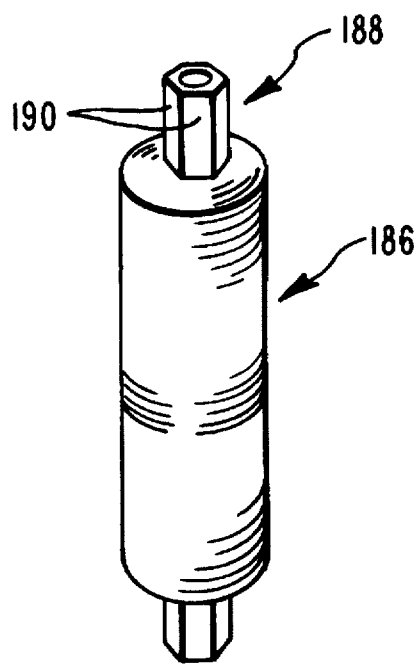
FIG. 18B shows an embodiment of an internal or a replacement spool of dental floss that has many paired parallel sides that can also be used with a slotted member locking means.

The replacement spools of floss depicted in FIGS. 18A and 18B show two different implementations of the multiple parallel sides that can be engaged by a slotted member. The internal spool 180 shows a minimal implementation of the parallel sides necessary for engagement. The end 182 is squared. The sides 184 are oriented such that there are two parallel sides that can be engaged.

FIG. 18B shows many parallel sides that can be engaged. Again, the internal spool of floss 186 has an end 188 that has thereon many sides 190. The advantage of having more parallel sides to be engaged by slotted member, is that finer increments of floss be dispersed.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A hand-held dental floss dispenser allowing a desired length of dental floss to be pulled through a dispersal aperture at which point the hand holding the dispenser is used to stop the dispersement of the floss so that the desired length of floss can be tensioned between the hand pulling the floss and the dispenser and flossing commences without separating the floss from the dispenser, the dental floss dispenser comprising:
   a) a dispenser body having a floss dispersal aperture, the body is capable of being gripped by the hand holding the dispenser so as to leave the thumb and forefinger free to manipulate the dispensed floss during flossing;
   b) a quantity of dispensable dental floss within the dispenser body, the dental floss exiting the dispenser body through the floss dispersal aperture;
   c) a floss securement means actuated by one or more of the lower three fingers of the hand holding the dispenser to lock the dental floss with respect to the dispenser body allowing the dental floss to be tensioned when pulled from the dental floss dispersal aperture by the hand pulling the dental floss from the dispenser.

2. A dental floss dispenser as in claim 1 wherein the dispenser body further comprises finger gripping means that allow the dispenser body to be held away from the palm of the hand by any one or more of the lower three fingers of the hand.

3. A dental floss dispenser as in claim 1 wherein the dispenser body is contoured to fit matingly within the hand of the user.

4. A dental floss dispenser as in claim 1 wherein the dispenser body has an upper end, the upper end being U-shaped having a first prong and a second prong, the first and second prongs forming an indentation to allow quick grasping of the dental floss strung from the floss dispersal aperture on the first prong of the U-shaped end to a floss cutter, placed on the second prong of the U-shaped end, the indentation configured so that a finger of the hand pulling the dental floss may readily grasp the floss at the desired location on the finger without further positioning the floss.

5. A dental floss dispenser as in claim 4 wherein the second prong of the U-shaped end is trough-shaped and the cutter is at the bottom area of the trough.

6. A dental floss dispenser as in claim 4 wherein the second prong of the U-shaped end is sloped and the cutter is placed at the bottom of the sloped second prong and the floss dispersal aperture is placed in a correspondingly forward position on the first prong to encourage movement of the floss towards the cutter.

7. A dental floss dispenser as in claim 1 wherein the floss securement means comprises a pinching means to bind the floss with respect to the dispenser body.

8. A dental floss dispenser as in claim 1 wherein the floss securement means comprises a pinching means that frictionally engages the floss until it is secured with respect to the dispenser body.

9. A dental floss dispenser as in claim 1 wherein the quantity of dispensable dental floss comprises a freely rotatable spool of dental floss rotatably within the dispenser body and capable of being locked into a stationary position with respect to the dispenser body and the floss securement means comprises locking the freely rotatable spool into a stationary position relative to the dispenser body.

10. A dental floss dispenser as in claim 9 wherein the securement means comprises frictionally engaging the spool of dental floss to secure the floss with respect to the dispenser body.

11. A dental floss dispenser as in claim 9 wherein the dispenser body is made of squeezable material and the dispenser body has an internal surface capable of frictionally engaging the freely rotatable spool of dental floss and the freely rotatable spool is locked by squeezing the dispenser body until the internal surface of the dispenser body sufficiently engages the freely rotatable spool of dental floss so that it is locked into a stationary position relative to the dispenser body.

12. A dental floss dispenser as in claim 9 wherein the freely rotatable spool further comprises at least one end having locking holes and the floss securement means further comprising:
   a) a lock member actuator operably external to the dispenser body that is actuated by the hand holding the dispenser; and
   b) a rod for insertion into the locking holes that is attached to the lock member actuator and passes through the dispenser body to lockingly engage the locking holes and lock the freely rotatable spool into a stationary position relative to the dispenser body causing the floss to be secured with respect to the dispenser body.

13. A dental floss dispenser as in claim 9 wherein the freely rotatable spool further comprises at least one end having multiple parallel sides and the floss securement means further comprising:
   a) a lock member actuator operably external to the dispenser body that is hand actuated by the hand holding the dispenser; and
   b) a lock member operably attached to the lock member actuator the lock member having a bore adapted for allowing the freely rotatable spool to freely rotate and having a slot immediately connected to the bore, the slot capable of tightly engaging any two of the parallel sides of the end of the freely rotating spool such that when so engaged the freely rotating spool is locked in relative position to the dispenser body causing the floss to be secured with respect to the dispenser body.

14. A dental floss dispenser as in claim 9 further comprising braking means for providing graduated and controlled resistance to the dental floss as it is pulled from the dispersal aperture.

15. A dental floss dispenser as in claim 1 wherein the dispenser body further comprises a stabilizing base that is wider than the dispenser body to facilitate a user quickly grabbing or releasing said floss dispenser onto a flat surface with only one hand without tipping said floss dispenser.

16. A hand-held dental floss dispenser allowing a desired length of dental floss to be pulled through a dispersal aperture at which point the hand holding the dispenser is used to stop the dispersement of the floss so that the desired length of floss can be tensioned between the hand pulling the floss and the dispenser and flossing commences without separating the floss from the dispenser, the dental floss dispenser comprising:
   a) a dispenser body having a floss dispersal aperture, the body capable of being gripped by the hand holding the dispenser so as to leave the thumb and forefinger free to manipulate the dispensed floss;
   b) a freely rotatable spool of dental floss rotatably within the dispenser body and capable of being locked into a stationary position with respect to the dispenser body and the dental floss exiting the dispenser body through the floss dispersal aperture;
   c) a spool locking means, actuated by one or more of the lower three fingers of the hand holding the dispenser, to lock the freely rotatable spool into a stationary position relative to the dispenser body allowing the dental floss to be tensioned when pulled from the dental floss dispersal aperture by the hand pulling the dental floss from the dispenser.

17. A dental floss dispenser as in claim 16 wherein the freely rotatable spool has at least one end having axially opposed multiple parallel sides and the locking means comprises a lock member having a bore for allowing the spool to freely rotate and a slot formed by parallel internal sides for engaging any of the axially opposed multiple parallel sides of the spool end to lock the spool with respect to the dispenser body.

18. A dental floss dispenser as in claim 16 where the spool has at least one end having holes and the locking means comprises a rod to engage the holes of the spool end to lock the spool with respect to the dispenser body.

19. A hand-held dental floss dispenser allowing a desired length of dental floss to be pulled through a dispersal aperture at which point the hand holding the dispenser is used to stop the dispersement of the floss so that the desired length of floss can be tensioned between the hand pulling the floss and the dispenser and flossing commences without separating the floss from the dispenser, the dental floss dispenser comprising:
   a) a dispenser body having a floss dispersal aperture, the body capable of being gripped by the hand holding the dispenser so as to leave the thumb and forefinger free to manipulate the dispensed floss;
   b) a quantity of dental floss within the dispenser body, the floss exiting out through the floss dispersal aperture; and
   c) a means for controlling the movement of the dental floss through the floss dispersal aperture comprising:
      (i) at least one of the lower three fingers of the hand holding the dispenser at a first position; and
      (ii) a second position that has the finger or fingers in a position closer to the palm of the hand than when at the first position, said first and second positions used to control movement of the dental floss through the floss dispersal aperture.

20. A dispenser as recited in claim 19 wherein the floss dispersal aperture is configured so that the dental floss exits between the thumb and forefinger of the hand holding the dispenser.

21. A spool of dental floss for use in a hand-held dental floss dispenser allowing a desired length of dental floss to be pulled through a dispersal aperture at which point the hand holding the dispenser is used to stop the dispersement of the floss so that the desired length of floss can be tensioned between the hand pulling the floss and the dental floss dispenser, the spool comprising:
   a) an elongated member having a middle section and two ends, at least one of the ends having a locking shape means comprising axially opposing multiple parallel sides for locking the spool within the dental floss dispenser; and
   b) a quantity of dental floss wrapped around the middle section.

22. A spool of dental floss for use in a hand-held dental floss dispenser allowing a desired length of dental floss to be pulled through a dispersal aperture at which point the hand holding the dispenser is used to stop the dispersement of the floss so that the desired length of floss can be tensioned between the hand pulling the floss and the dental floss dispenser, the spool comprising:
   a) an elongated member having a middle section and two ends, at least one of the ends having a locking shape means comprising holes for locking the spool within the dental floss dispenser; and
   b) a quantity of dental floss wrapped around the middle section.

* * * * *